United States Patent [19]

Didillon et al.

[11] Patent Number: 5,118,884
[45] Date of Patent: Jun. 2, 1992

[54] HYDROGENATION OF CITRAL

[75] Inventors: Blaise Didillon, Lyons; Jean-Pierre Candy, Caluire; Jean-Marie Bassett, Villeurbanne; Jean-Paul Bournonville, Cergy Pontoise, all of France

[73] Assignee: Institut Francais du Petrole, Rueil Malmaison, France

[21] Appl. No.: 578,113

[22] Filed: Sep. 6, 1990

[30] Foreign Application Priority Data

Oct. 13, 1989 [FR] France ................. 89 13518

[51] Int. Cl.$^5$ .................. C07C 29/141; C07C 33/02
[52] U.S. Cl. .................... 568/875; 502/242
[58] Field of Search ......................... 568/875

[56] References Cited

U.S. PATENT DOCUMENTS

| 3,919,187 | 11/1975 | Bourdoncle et al. | 260/125 |
| 4,029,709 | 6/1977 | De Simone et al. | 568/875 |
| 4,073,813 | 2/1978 | Cordier | 568/875 |
| 4,100,180 | 7/1978 | Ichikawa et al. | 508/857 |
| 4,361,500 | 11/1982 | Màthe et al. | 252/430 |
| 4,455,442 | 6/1984 | Horner et al. | 568/875 |
| 4,465,787 | 8/1984 | Horner et al. | 502/185 |
| 4,536,347 | 8/1985 | Horner et al. | 260/465 F |

FOREIGN PATENT DOCUMENTS 3825654 12/1963 Japan .................. 568/875

OTHER PUBLICATIONS

Ichikawa et al, "Chem. Abstracts" vol. 83 (1975) p. 393, col. 1, 192552q.

Primary Examiner—J. E. Evans
Attorney, Agent, or Firm—Millen, White & Zelano

[57] ABSTRACT

The invention concerns the production of a diolefinic unsaturated alcohol such as geraniol or nerol by the selective hydrogenation of citral. It is characterized by the use of a catalyst based on a metal from group VIII and based on a metal selected from the group made up of tin, germanium and lead, on preferably a silica carrier.

8 Claims, No Drawings

HYDROGENATION OF CITRAL

BACKGROUND OF THE INVENTION

The invention concerns a method of producing unsaturated diolefinic alcohols (particularly geraniol and nerol) by selective hydrogenation of citral.

Citral is an aldehyde containing two olefinic carbon-carbon bonds and is of the following total formula:

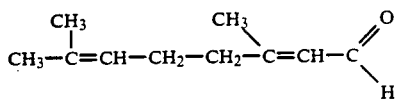

3,7 dimethyl 2,6 octadiene-al or citral ($C_{10}H_{16}O$).

Selective hydrogenation of the aldehyde function leads to the formation of unsaturated isomeric alcohols such as geraniol and nerol, which both have the following total developed formula:

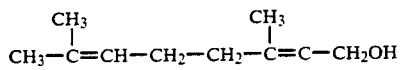

3,7 dimethyl 2,6 octadiene-1 ol (nerol or geraniol).

These materials are used particularly in the perfume industry.

It is very difficult with this reaction is to obtain high and, if possible, total conversion with the best possible selectivity, i.e. as close as possible to 100%, for diolefinic alcohols. The isomeric diolefinic alcohols, geraniol and nerol, may in turn undergo partial or total hydrogenation of the double olefinic bonds, to give the following two products: firstly

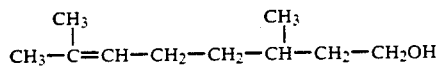

3,7 dimethyl-6 octene-1 ol or citronellol in the case of hydrogenation of the double bond located at α in the alcohol function secondly

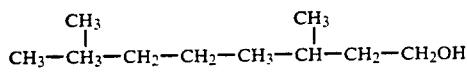

3,7 dimethyl octanol 1 when all the unsaturated carbon-carbon and carbon-oxygen bonds are hydrogenated.

The double olefinic bond conjugated with the aldehyde function may also be hydrogenated to give a compound of the following total formula:

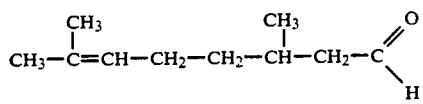

3,7 dimethyl 7-octenal or citronellal which, after hydrogenation of the double olefinic bond, gives 3,7 dimethyl octanal.

The group VIII metals are known as catalysts for converting citral under hydrogen pressure and in liquid phase, that is to say in the presence of a solvent. Thus selective hydrogenation of citral to citronellal has been claimed in the presence of catalysts based on palladium (EP-A-008741 and FR-B-2405232), as has been claimed hydrogenation of citral to 3,7 dimethyl octanal (DE 2832699). Cobalt and nickel chlorides, associated in solution with potassium cyanide and an aliphatic amine, also enable very high yields of citronellal to be obtained from citral under hydrogen pressure (SU958.408).

The conversion of citral to citronellol is described in a number of publications. Thus a 93% yield of citronellol is obtained under hydrogen pressure from citral in the presence of a catalyst containing palladium associated with iridium, osmium, platinum, rhodium or ruthenium and with an aliphatic amine (DE 293250). Nickel, rhodium, platinum or palladium in solid form enable citronellol to be produced from citral with selectivities of over 90% (Kinet. Catal 21(3), 670-5). Nickel deposited on chromium oxide, in an alcoholic medium and in the presence of sodium carbonate, enables 95% yields of citronellol to be obtained from citral (Reaction Kinetics and Catalysis Letters, 16(4), 339-43).

As far as selective hydrogenation of citral to geraniol and nerol in liquid phase ($CH_3OH$) is concerned, the obtaining of high selectivities (93-95%) with limited conversion has been claimed (U.S. Pat. No. 4,100,180) in the presence of platinum oxide $PtO_2$ promoted by $FeSO_4$ and Zn ($CH_3COO$)$_2$. The catalyst may be reused, provided that the iron and zinc compounds are added with each citral charge. Similarly, a platinum based catalyst supported on charcoal will give high selectivities for geraniol and nerol (over 95%) with 92 and 97% citral conversions (U.S. Pat. No. 4073813). Finally, two patents in the name of BASF AG claim the use of catalysts, one containing 5% by weight of Pd, Ir, Os, Rh, Ru or Pt supported on charcoal in the presence of an aliphatic amine (U.S. Pat. No. 4,455,442), and the other containing 5% of ruthenium supported on charcoal promoted by iron, also in the presence of an aliphatic amine (U.S. Pat. No. 4,465,787). The catalysts have high activity and selectivity but require well-defined additions of chemical compounds.

SUMMARY

It has been discovered in the present invention that it is possible to carry out selective hydrogenation of the citral or 3,7 dimethyl 20 octadienal to geraniol or nerol, with reduced production of citronellal. The operation takes places in a continuous or discontinuous reactor in the presence of hydrogen, at a total pressure of from 10 to 100 bars (1 to 10 Megapascals) and preferably from 20 to 80 bars (2 to 8 Megapascals), or preferably above 30 bars (3 Megapascals), although one can operate e.g. up to 300 bars (30 Megapascals) without any trouble, at a temperature from 0 to 100 degrees Celsius and preferably from 30 to 80 degrees Celsius, in the presence of a supported metal catalyst containing (a) at least one group VIII metal selected from iridium, platinum, rhodium and ruthenium (rhodium and ruthenium being the preferred metals), the percentage by weight of the metal being selected from 0.1 to 10% and preferably from 0.5 to 5% and (b) at least one additional element selected from group IV.A consisting of tin, germanium and lead, the percentage by weight thereof being selected from 0.01 to 10% and preferably from 0.1 to 5%. The molar ratio of group IV metal element to group VIII metal is advantageously from 0.8:1 to 3:1 and preferably from 0.9:1 to 2.6:1. In some cases two of the metals in group IV-A above or even all three metals may advantageously be used simultaneously; when a carrier is used it may be selected from the group made up of silica, the various types of alumina, alumina silicas, aluminates of the elements in groups $I_A$, $II_A$, or $II_B$ of the Periodic Table of Elements, for example aluminates of Ca, Mg, Ba, Zn, Na, K or Cd, combined aluminates and charcoal, preferably from the group comprising silica, alkali metal and/or alkaline earth metal and/or zinc and/or cadmium aluminates and combined aluminates, and still more preferably a carrier based on silica.

The catalyst may be prepared by various procedures for impregnating the carrier, and the invention is not restricted to any specific procedure. The impregnating operation may e.g. comprise putting the preformed carrier into contact with an aqueous or organic solution of a compound of the selected metal or metals, the volume of solution preferably being in excess of the retention volume of the carrier or equal to that volume. The group VIII metal and the additional metal may be added simultaneously or successively. When the carrier has been left in contact with the solution for some hours, the impregnated carrier is filtered, washed with distilled water, dried and calcined in air, usually from 110° to 600° C. and preferably from 110° to 500° C. Before the catalyst is used it is reduced in hydrogen, usually at from 50° to 600° C. and preferably from 90° to 500° C. Reduction may be carried out immediately after calcination or later by the user.

The element selected from the group made up of tin, germanium and lead may be introduced in aqueous solution or in hydrocarbon solution, according to the nature of the precursor used.

The catalyst is preferably obtained by impregnating the carrier with an aqueous or organic solution of at least one compound of group VIII metal, the volume of solution preferably being in excess of the retention volume of the carrier or equal to that volume. The impregnated carrier is then filtered, possibly washed with distilled water, then dried and calcined in air, usually at from about 110° to about 600° C. and preferably from about 110° to about 500° C.; it is then reduced in hydrogen to a temperature usually from about 200° to about 600° C. and preferably from about 400° to about 500° C. The product obtained is then impregnated with an aqueous or organic solution of a germanium, tin and/or lead compound. It is particularly advantageous to use a solution of at least one hydrocarbyl-germanium, hydrocarbyl-tin or hydrocarbyl-lead in a saturated hydrocarbon, using the technology described in U.S. Pat. No. 4,548,918.

Of the organic solvents which can be used in the invention, hydrocarbons, halogenated hydrocarbons, ketones and ethers may be mentioned as non-restrictive examples. It is not essential to use a solvent when the germanium, tin and/or lead compound is liquid itself, as is the case e.g. with tetrabutyltin.

When the carrier impregnated with the Group VIII metal has been left in contact with the solution containing at least one germanium, tin or lead compound for a few hours, the product is filtered, possibly washed with the solvent used to deposit the germanium, tin and/or lead, dried and possibly calcined in air, usually at from about 110° to about 600° C. and preferably from about 110° to 500° C. Before the catalyst is used it is reduced in hydrogen, usually at from about 50° to about 600° C. and preferably from about 90° to about 500° C. Reduction may be carried out immediately after calcination or later by the user.

Another method comprises mixing the moist carrier powder with the catalyst precursors, then shaping and drying them.

Examples of the metal precursors which can be used in preparing the catalysts are as follows:

For the group VIII metal one can use compounds such as nitrates, chlorides, halo-ammino compounds, ammino compounds or salts of organic acids which are soluble in the impregnating solvent.

It is also possible to use organometallic compounds of a group VIII metal in solution in an organic solvent such as a hydrocarbon. Some examples of hydrocarbons are saturated paraffinic hydrocarbons in which the hydrocarbon chain contains 6 to 12 carbon atoms per molecule, naphthene hydrocarbons containing 6 to 12 carbon atoms per molecule or aromatic hydrocarbons containing 6 to 11 atoms per molecule. Some examples of organometallic compounds of group VIII metal are carbonyl and halogenocarbonyl compounds and acetylacetonates; but the invention is not restricted to this list.

The element selected from the group made up of tin, germanium and lead may be introduced preferably in the form of at least one organic compound from the group formed by complexes, particularly polyketone complexes, of metals from group IV.A and hydrocarbyl metals such as alkyl, cycloalkyl, aryl, alkylaryl and arylalkyl metals.

The IV.A metal is advantageously introduced in solution in an organic solvent of the organometallic compound of the IV.A metal. Organic halogenated compounds of the IV.A metals may equally be used. Particular examples of the IV.A metal compounds are tetrabutyltin, tetramethyltin, tetrapropyltin, tetrapropylgermanium, tetraethyllead, diphenyltin, diphenylgermanium and tetraphenyllead.

The impregnating solvent is chosen from the group comprising paraffinic, naphthenic or aromatic hydrocarbons containing 6 to 12 carbon atoms per molecule and organic halogenated compounds containing 1 to 12 carbon atoms per molecule. Some examples are n-heptane, methylcyclohexane, toluene and chloroform. Mixtures of the above solvents may also be used.

The element selected from the group made up of tin, germanium and lead may also be introduced in the form of compounds such as tin chlorides, bromides and nitrate, lead halides, nitrate and acetate and germanium chloride and oxalate, in aqueous or organic solution.

The carrier may be of various types, as already mentioned, but it is preferably based on silica. A particularly appropriate carrier has specific characteristics such as a specific surface area, determined by the B.E.T. method, of from 10 to 500 $m^2/g$ and preferably from 50 to 500 $m^2/g$, and a total pore volume of 0.2 to 1.3 $cm^3$ per gram of carrier.

Once the metals have been fixed on the carrier, the catalyst advantageously undergoes activating treatment in hydrogen at high temperature, e.g. from 50° to 600° C., in order to obtain an active metal phase. The procedure for the hydrogen treatment may e.g. comprise a slow rise in temperature in a stream of hydrogen up to the maximum reduction temperature e.g. from 50° to 600° C. and preferably from 90° to 500° C. after which the temperature is kept at that level e.g. for 1 to 6 hours.

The following examples are given to illustrate the invention but the invention is not restricted to these.

EXAMPLE 1

The catalyst is prepared in two stages:
the rhodium is first fixed by impregnating rhodium chloropentammine chloride in an ammoniacal solution on a silica with a specific surface area of 280 m² per gram and a total pore volume of 80 cm³ per 100 grams, followed by filtration, drying at 110° C., calcination in air at 450° C. and reduction in hydrogen at 450° C.

the catalyst is then placed in a Guignard type reactor containing an organic solvent, normal hexane. The tetrabutyl-tin is then injected into the solvent and the reactor is closed. The hydrogen pressure is increased to 40 bars (4 Megapascals) and the temperature raised to 96° C. These conditions are maintained for twenty minutes with agitation.

The initial monometallic catalyst (that is to say, without the addition of tin) contains 1.3% by weight of rhodium.

A series of catalysts containing different concentrations of tin is prepared by the method described above. The composition of the catalysts is given in Table 1.

TABLE 1

| Catalyst | % Rh (wt) | % Sn (wt) | Sn/Rh molar | Sn/Rh by weight |
|---|---|---|---|---|
| A | 1.3 | 0.75 | 0.1 | 0.11 |
| B | 1.3 | 0.75 | 0.5 | 0.57 |
| C | 1.3 | 1.5 | 1.0 | 1.15 |
| D | 1.3 | 3.75 | 2.5 | 2.88 |

EXAMPLE 2

The catalysts of Example 1 are then tested in the citral hydrogenation reaction under the following operating conditions:
temperature: 65° C.
hydrogen pressure = 76 bars (7.6 Megapascals)
citral/rhodium ratio = 200:1.

The testing procedure is as follows:
when the tetrabutyl tin has reacted under the conditions described in Example 1, the pressure in the reactor is brought back to atmospheric and the temperature lowered to 25° C.,
a solution of citral in n-hexane is then injected into the reactor in a proportion of 200 molecules of diolefinic aldehyde (citral) per gram atom of rhodium. After purging with hydrogen, the hydrogen pressure is raised to the desired level (here 76 bars) and so is the temperature (65° C.). The results given in Table 2 are obtained after 5 hours of operation.

TABLE 2

| Catalyst | Conversion (% by wt) | Selectivity (% by wt) | | | |
|---|---|---|---|---|---|
| | | Citronellol | Citronellal | Geraniol nerol | 3,7 DMe octanol |
| A | 100.0 | 12.8 | 81.0 | 6.2 | — |
| B | 91.4 | 16.9 | 13.7 | 69.3 | — |
| C | 95.7 | 5.4 | — | 94.6 | — |
| D | 100.0 | 3.5 | — | 96.5 | — |

The increase in the tin content (or more accurately the tin/rhodium ratio) thus brings a very substantial improvement in selectivity for geraniol and nerol.

EXAMPLE 3

After hydrogenation of citral in the presence of catalyst D, the pressure in the reactor is lowered to atmospheric and the reactor is emptied of the liquid phase containing the solvent and the products of hydrogenation. A new citral charge, diluted with n-hexane, is then injected into the reactor and the hydrogen pressure and temperature are adjusted to the same values as in Example 2. After 5 hours the products of the reaction are analyzed. The operation can then be repeated as desired.

The results of 5 successive hydrogenations with the same catalyst charge are given in Table 3.

TABLE 3

| Hydrogenation | Conversion (% by wt) | Selectivity (% by wt) | | | |
|---|---|---|---|---|---|
| | | Citronellol | Citronellal | Nerol geraniol | 3,7 DMe octanol |
| 1st | 100.0 | 3.5 | — | 96.5 | — |
| 2nd | 100.0 | 3.8 | — | 96.2 | — |
| 3rd | 100.0 | 3.4 | — | 96.6 | — |
| 4th | 100.0 | 4.1 | — | 95.9 | — |
| 5th | 100.0 | 3.6 | — | 96.4 | — |

The same catalyst charge can thus be used several times running without any significant change in its catalytic properties.

EXAMPLE 4

Catalyst C is used under the conditions in Example 2, except that the reaction temperature is adjusted to 51° C. After 5 hours of reaction the reaction products are analyzed. The results are as follows:
conversion of citral: 100%
selectivity (% by weight):
citronellol: 5.6
citronellal: -
geraniol and nerol: 94.4
3,7 dimethyloctanol: -
The results are close to those in Example 2

EXAMPLE 5

Catalyst C is used under the conditions of Example 2, except that the reaction temperature is kept at 20° C. In this case the reaction has to be continued for 16 hours in order to achieve total conversion of the citral. When the reaction products are analyzed, the results can be expressed as follows:
conversion of citral: 100%
selectivity (% by weight)
3,7 dimethyl octanol: -
citronellal: -
citronellol: 8.0
geraniol and nerol: 92.0
The drop in temperature increases the reaction time required to achieve a total conversion, which is less favorable to selectivity as compared with Example 2, although very acceptable.

EXAMPLE 6

Catalyst C is used with the operating procedure described in Example 2, except that the temperature and hydrogen pressure are adjusted respectively to 20° C. and 20 bars (2 Megapascals).

After 15 hours of reaction and analysis of the reaction medium, the results are then:
conversion of citral: 39.4%
selectivity (% by weight):
3,7 dimethyl octanol: -
citronellol: -
citronellal: 5.6
geraniol-nerol: 94.4

The reduction in pressure together with the reduction in temperature does not improve selectivity but reduces the activity of the catalyst. Hence it is prefera-

EXAMPLE 7

Catalyst A is used under the conditions of Example 5. When the reaction products have been analyzed the results, after 15 hours, are as follows:
conversion of citral (%): 100%
selectivity (% by weight):
3,7 dimethyl octanol: -
citronellol: 18.4
citronellal: 81.6
geraniol and nerol: -

If these are compared with Example 2, it will be seen that the formation of both 3,7 dimethyl octanol and geraniol and nerol can be avoided by adjusting the temperature.

EXAMPLE 8

A catalyst based on ruthenium instead of rhodium is also prepared, using the following procedure:
fixing the ruthenium by impregnating ruthenium chloropentammine chloride in ammoniacal solution on a silica with a specific surface area of 280 $m^2$ per gram and a total pore volume of 80 $cm^3$ per 100 grams, followed by filtration, drying at 110° C., calcination in air at 450° C. and reduction in hydrogen at 450° C. The catalyst contains 1% by weight of ruthenium.

It is put into contact with tetrabutyl tin under the same conditions as in Example 1.

Two catalysts are prepared in this way:

|  | Sn/Ru | |
| --- | --- | --- |
|  | molar | weight |
| catalyst E: 1% Ru 1.2% Sn | 1 | 1.2 |
| catalyst F: 1% Ru 2.9 Sn | 2.45 | 2.9 |

The catalysts are tested under the conditions of Example 2, a hydrogen pressure of 76 bars (7.6 Megapascals) and a temperature of 65° C.

After 7 hours the results are as follows:

| Catalyst | Conversion of citral/ % by weight | Selectivity (% by wt) | | |
| --- | --- | --- | --- | --- |
|  |  | 3,7 DMe octanol | Citronellol | Citronellal | Geraniol nerol |
| E | 99.8 | — | 6.2 | — | 93.8 |
| F | 99.9 | — | 4.0 | — | 96.0 |

EXAMPLE 9

Using the monometallic catalyst based on a group VIII metal prepared by the procedure described in Example 1 for Rh and in Example 8 for Ru, it is proposed to prepare bimetallic catalysts in which the tin is replaced by tetrabutyl germanium and tetrabutyl lead.

The second group IV metal (germanium or lead) is fixed under the same conditions as described in Example 1.

The composition of the catalysts prepared is given in Table 4:

| Catalyst | % of Group VIII metal | % of promoting metal | IV/VII molar | weight |
| --- | --- | --- | --- | --- |
| G | Ru: 1.1 | Ge: 1.55 | 2.1 | 1.41 |
| H | Ru: 1.1 | Pb: 4.40 | 2.1 | 4 |
| J | Ru: 1.0 | Ge: 1.44 | 2.0 | 1.44 |
| K | Ru: 1.0 | Pb: 4.10 | 2.0 | 4.10 |

These catalysts are used in the citral hydrogenating reaction under the same conditions as in Example 2.

After 8 hours of reaction the results are as follows:

| Catalyst | Conversion of citral/ % by weight | Selectivity (% by wt) | | | |
| --- | --- | --- | --- | --- | --- |
|  |  | 3,7 DMe octanol | Citronellol | Citronellal | Geraniol nerol |
| G | 99.8 | — | 4.1 | — | 95.9 |
| H | 99.1 | — | 5.0 | — | 95.0 |
| J | 99.5 | — | 4.6 | — | 95.4 |
| K | 98.8 | 0.01 | 5.5 | — | 94.5 |

EXAMPLE 10

A monometallic catalyst based on Ru is prepared by the procedure described in Example 8, but with two different carriers: active carbon and alumina.

The carriers have the following properties:
specific surface area:
200 $m^2$ per gramme for alumina
850 $m^2$ per gramme for carbon
pore volume:
60 $cm^3$ per 100 grammes for alumina
80 $cm^3$ per 100 grammes for carbon.

The tin is fixed under the same conditions as are described in Example 1.

Two catalysts are thus prepared:

|  | Sn/Ru | |
| --- | --- | --- |
|  | molar | weight |
| Catalyst L (on active carbon) 1% Ru; 2.9% Sn | 2.45 | 2.9 |
| Catalyst M (on alumina) 1% Ru; 3% Sn | 2.50 | 3.0 |

The catalysts are comparable with catalysts F (on a silica carrier) in Example 8.

They are tested under the conditions in Example 2.
After 7 hours of reaction the results are as follows:

|         | Conversion of citral/ | 3,7 DMe 2,6 | Selectivity (% by wt) | | | |
|---------|----------------------|-------------|-------------|-------------|----------|----------|
| Catalyst | % (by weight)       | octadiene   | Citronellol | Citronellal | 3,7 Dme 6 octene | Geraniol nerol |
| F       | 99.9                 | —           | 4.0         | —           | —        | 96.0     |
| L       | 90.0                 | —           | 6.5         | —           | —        | 93.5     |
| M       | 95.0                 | 7           | 2.5         | —           | 1.5      | 89       |

It will be seen that a large amount of dehydration products (3,7-dimethyl-2,6 octadiene and 3,7-dimethyl-6 octene) are formed with catalyst M.

EXAMPLE 11

A monometallic catalyst based on Ru is prepared by the procedure described in Example 8, but with two different carriers, active carbon and alumina.

The lead is fixed under the same conditions as are described in Example 1.

Two catalysts are prepared in this way, comparable with catalyst K in Example 9 (with a silica carrier):

|  | Pb/Ru | |
|---|---|---|
|  | molar | weight |
| Catalyst L (on active carbon) 1% Ru; 4.4% Pb | 1.95 | 4 |
| Catalyst P (on alumina) 1% Ru; 4.1% Pb | 2.0 | 4.10 |

They are tested under the conditions in Example 2. After 8 hours of reaction, the results are as follows:

|         | Conversion of citral/ | 3,7 DMe 2,6 | Selectivity (% by wt) | | | |
|---------|----------------------|-------------|-------------|-------------|----------|----------|
| Catalyst | % (by weight)       | octadiene   | Citronellol | Citronellal | 3,7 Dme 6 octene | Geraniol nerol |
| K       | 98.8                 | —           | 5.5         | —           | —        | 94.5     |
| N       | 88.0                 | —           | 7.5         | —           | —        | 92.5     |
| P       | 97.0                 | 9           | 3           | —           | 2        | 86       |

It will be observed that a large amount of dehydration products (3,7-dimethyl-2,6 octadiene and 3,7-dimethyl-6 octene) are formed with catalyst P.

We claim:

1. A method of producing at least one diolefinic alcohol by selective hydrogenation of citral, wherein the method takes place under a pressure of over 10 bars, at a temperature of 0°–100° C., and in the presence of at least one catalyst on a silica based carrier, containing:
   (a) 0.1 to 10% by weight of at least one group VIII metal, said group VIII metal being rhodium or ruthenium, and
   (b) 0.01 to 10% (expressed as metal) by weight of at least one additional element based on a group IVA metal, said group IVA metal being tin, germanium or lead, said method resulting in at least one of: a higher conversion of citral and a higher selectivity for geraniol and nerol than that obtainable with the same method but using alumina or active carbon as a catalyst.

2. The method of claim 1, wherein the catalyst contains (by weight) 0.5 to 5% of said at least one group VIII metal and 0.1 to 5% (expressed as metal) of said at least one additional element based on a group IVA metal.

3. The method of claim 1, wherein the molar ratio of the group IVA metal to the group VIII metal is from 0.8:1 to 3:1.

4. The method of claim 3, wherein said ratio is from 0.9:1 to 2.6:1.

5. The method of claim 1, wherein the pressure is from 10 to 100 bars (1 to 10 Megapascals).

6. The method of claim 5, wherein the pressure is from 20 to 80 bars (2 to 8 Megapascals) and the temperature from 30° to 80° C.

7. The method of claim 1, wherein the group VIII metal is rhodium.

8. The method of claim 1, wherein the group VIII metal is ruthenium.

* * * * *